(12) United States Patent
Hunter et al.

(10) Patent No.: US 11,944,668 B2
(45) Date of Patent: Apr. 2, 2024

(54) ENZYME COMPOSITIONS AND DIAGNOSTICS FOR USE IN ENTEROMETABOLIC DYSFUNCTION

(71) Applicant: PEPSIS LIMITED, Ledbury (GB)

(72) Inventors: John Hunter, Ledbury (GB); Rosemary Waring, Ledbury (GB)

(73) Assignee: PEPSIS LIMITED, London (GB)

( * ) Notice: Subject to any disclaimer, the term of this patent is extended or adjusted under 35 U.S.C. 154(b) by 145 days.

(21) Appl. No.: 16/327,393

(22) PCT Filed: Aug. 23, 2017

(86) PCT No.: PCT/GB2017/052481
§ 371 (c)(1),
(2) Date: Feb. 22, 2019

(87) PCT Pub. No.: WO2018/037225
PCT Pub. Date: Mar. 1, 2018

(65) Prior Publication Data
US 2021/0052707 A1    Feb. 25, 2021

(30) Foreign Application Priority Data

Aug. 24, 2016 (GB) .................................. 1614415

(51) Int. Cl.
A61K 38/46 (2006.01)
A61P 1/14 (2006.01)

(52) U.S. Cl.
CPC ............... *A61K 38/46* (2013.01); *A61P 1/14* (2018.01)

(58) Field of Classification Search
CPC ................................. A61K 38/46; A61P 1/14
See application file for complete search history.

(56) References Cited

U.S. PATENT DOCUMENTS

| | | | |
|---|---|---|---|
| 6,558,666 B1 * | 5/2003 | Anderson | A61K 31/555 424/94.2 |
| 8,017,351 B2 * | 9/2011 | Svendsen | A61P 1/18 435/22 |
| 2005/0281795 A1 | 12/2005 | Jolly | |
| 2006/0115467 A1 | 6/2006 | Pangborn et al. | |
| 2009/0142315 A1 | 6/2009 | Farmer et al. | |
| 2009/0317371 A1 | 12/2009 | Arbab | |
| 2014/0154371 A1 * | 6/2014 | Mathys | A23L 2/48 426/582 |
| 2014/0314719 A1 | 10/2014 | Smith | |
| 2015/0196609 A9 * | 7/2015 | Smith | A61K 35/744 424/93.3 |

FOREIGN PATENT DOCUMENTS

| | | |
|---|---|---|
| AU | 2011204886 A1 | 8/2011 |
| GB | 2465814 A | 6/2010 |
| GB | 2468629 A | 9/2010 |
| GB | 2479294 A | 10/2011 |
| GB | 2507472 A | 5/2014 |
| WO | 2005098427 A2 | 10/2005 |
| WO | 2006136161 A2 | 12/2006 |
| WO | 2007059956 A1 | 5/2007 |
| WO | 2011000924 A1 | 1/2011 |
| WO | 2013136069 A2 | 9/2013 |
| WO | 2013155476 A1 | 10/2013 |
| WO | 2018096334 A1 | 5/2018 |

OTHER PUBLICATIONS

Zhang et al. Impacts of Gut Bacteria on Human Health and Diseases. Int. J. Mol. Sci. 2015;16:7493-7519.*
Osman AM. The advantages of using natural substrate-based methods in assessing the roles and synergistic and competitive interactions of barley malt starch-degrading enzymes. J. Inst. Brew. 2002;108(2):204-214.*
HealthyChildren. healthychildren.org. 2015;1-3.*
Wentzell et al. Mesentery Peritoneum. 2018;2:3:1-2.*
Enzymedica. Digest Basic. enzymedica.com. 2012;1-3.*
International Search Report and Written Opinion of Internatinal application No. PCT/GB2017/052481, dated Mar. 9, 2018, 21 pages.
Kei Nakajima Etal: "Low serum amylase in association with metabolic syndrome and diabete: A community-based study", Cardiovascular Diabetology, Biomed Central, London, GB, vol. 10, No. 1, Apr. 17, 2011, p. 34, XP021097806.
Database WPI, Week 201082, Thomson Scientific, London, GB; AN 2010-P06376, XP002776143, & CN101851651A (Univ Jiangnan) Oct. 6, 2010, abstract.
Corrected Search Report under Section 17 of Great Britain application No. GB1614415.6, dated Dec. 22, 2016, 3 pages.
European Examination Report for Patent Application No. 17758914.0 dated Mar. 18, 2021, 9 pages.
Proudman, C. J. et al., 'Characterisation of the faecal metabolome and microbiome of Thoroughbred racehorses', Equine Veterinary Journal (ISSN 0425-1644) DOI: 10.1111/evj.12324. (2014).
Walton, C. et al., 'Analysis of volatile organic compounds of bacterial origin in chronic gastrointestinal diseases', Inflammatory Bowel Diseases, 19, 2069-2078. (2013).
Batty, CA et al., "Use of the analysis of the volatile faecal metabolome in screening for colorectal cancer", PLoS, 10, 1-14, dd:10.137/journal.pone.0130301. (2015).
Walton, C. et al., 'Enteral feeding reduces metabolic activity of the intestinal microbiome in Crohn's disease: an observational study European Journal of Clinical Nutrition' 1-5, doi:10.1038/ejcn.2016.74. (2016).
Perry et al., "Acetate mediates a microbiome-brain-β-cell axis to promote metabolic syndrome", Nature 10.1038/nature18309. (2016).
Van der Waaij, LA, et al., "Immunoglobulin coating of faecal bacteria in inflammatory bowel disease", Eur. J. Gastroenterol. Hepatol., 16, 669-74. (2004).

(Continued)

*Primary Examiner* — Lynn Y Fan
(74) *Attorney, Agent, or Firm* — Maine Cernota & Curran

(57) ABSTRACT

The invention concerns the improvement of metabolic and digestive health of humans by providing diagnostic methods for enterometabolic disorders such as IBS and IBD and/or the treatment of IBS and IBD by compositions comprising enzyme rich malt extract (ERME).

3 Claims, 4 Drawing Sheets

(56) References Cited

OTHER PUBLICATIONS

Batty CA, et al., "Differences in microbial metabolites in urine headspace of subjects with immune thrombocytopaenia (ITP) detected by volatile organic compound (VOC) analysis and metabolomics", Clinica Chemica Acta, 461, 61-68. (2016).

Kavanagh R. et al., "The effects of elemental diet and subsequent food reintroduction on rheumatoid arthritis", British Journal of Rheumatology, 34, 270-3, (1995).

Altenbach et al., "Mutational Analysis of the Active Center of Plant Fructosyltranserases: Festuca 1-SST and Barley 6-SFT", FEBS Letters, 579, 21, 4647-4653. (2005).

Fava F. et al, "The type and quantity of dietary fat and carbohydrate alter faecal microbiome and short-chain fatty acid excretion in a metabolic syndrome 'at-risk' population", Int J Obesity. 37 216-223. (2013).

Boutagy NE et al., "Metabolic endotoxemia with obesity : is it real and is it relevant?", Biochimie 124 11-20. (2016).

Yamada T. et al., "Rapid and sustained long-term decrease of fecal short-chain fatty acids in critically ill patients with systemic inflammatory response syndrome", Japanese J. Parenteral and Enteral Nutrition 39(5) 569-77. (2015).

Simpson, HL and Campbell, BJ, "Dietary Fibre-microbiota Interactions", Alimentary Pharmacology and Therapeutics 42 (2) 158-179. (2015).

Sticher, L. "Isolation and Partial Characterization of a Factor from Barley Aleurone that Modifies α-Amylase in Vitro" in Plant Physiol. 1991; 97, 936-942.

Srivastava, R. "Effect of glycosylation of bacterial amylase on stability and active site conformation" in Indian Journal Biochem. and Biophysics, 1991; 28, 2, 109.

"Enzymes," Web page <http://web.fscj.edu/david.byres/enzyme1.html>, 3 pages, 2014, retrieved from Internet Archive Wayback Machine <https://web.archive.org/web/20201111234124/web.fscj.edu/david.byres/enzyme1.html> on Oct. 14, 2022.

EP Office Action for Application No. 17758914.0 dated Nov. 23, 2023, 7 pages.

* cited by examiner

Figure 1 - Faecal Acetate measurements of ERME
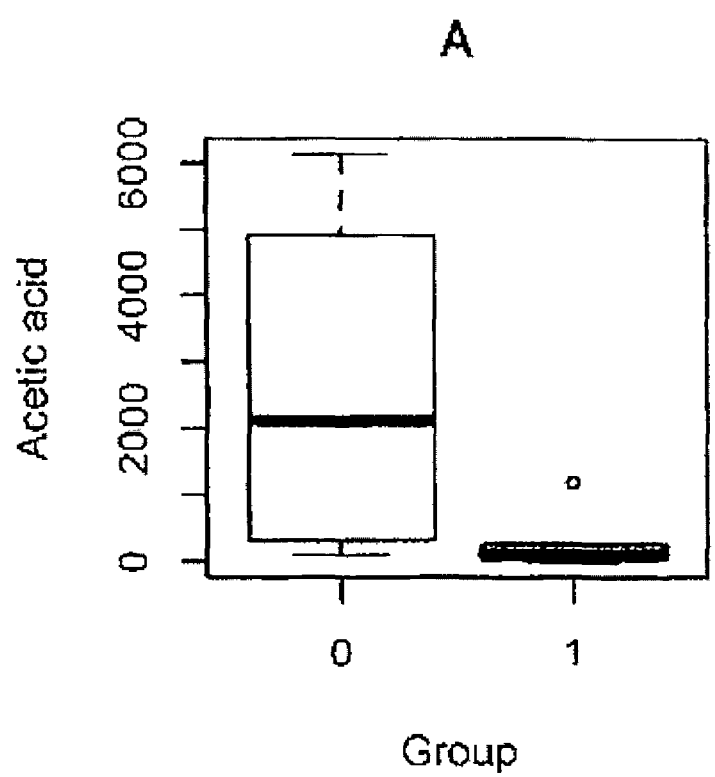

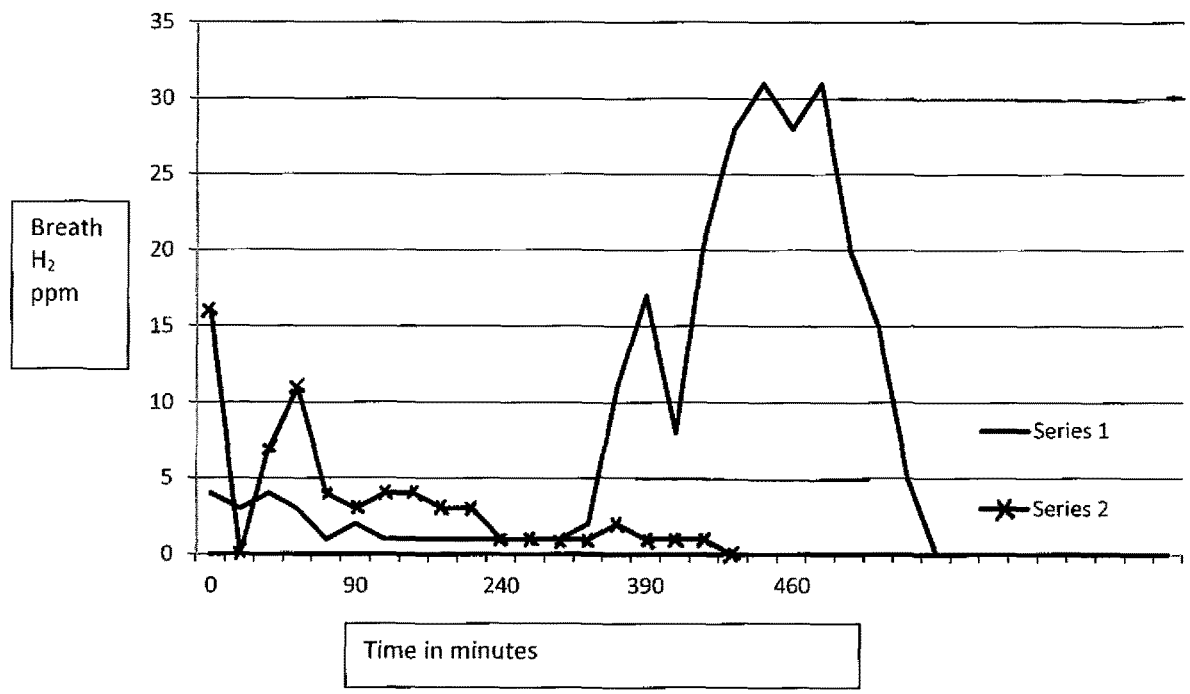
Figure 2 – IBS patient with and without ERME treatment

Figure 3 – Breath hydrogen concentrations of IBS and healthy subjects and treatment with ERME
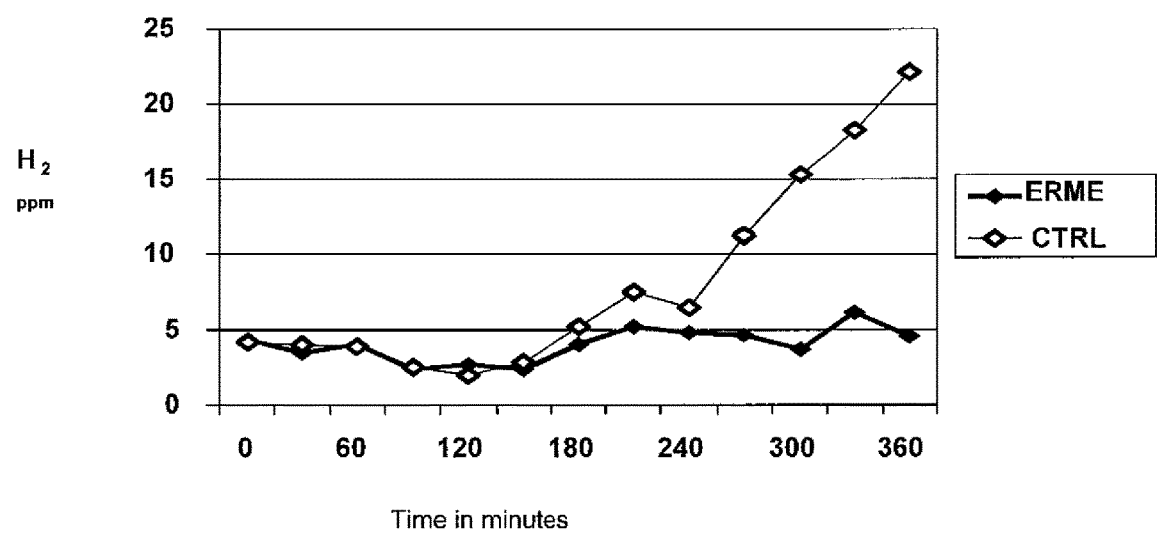

Figure 4 – Mean breath hydrogen excretion IBS vs healthy (no treatment)
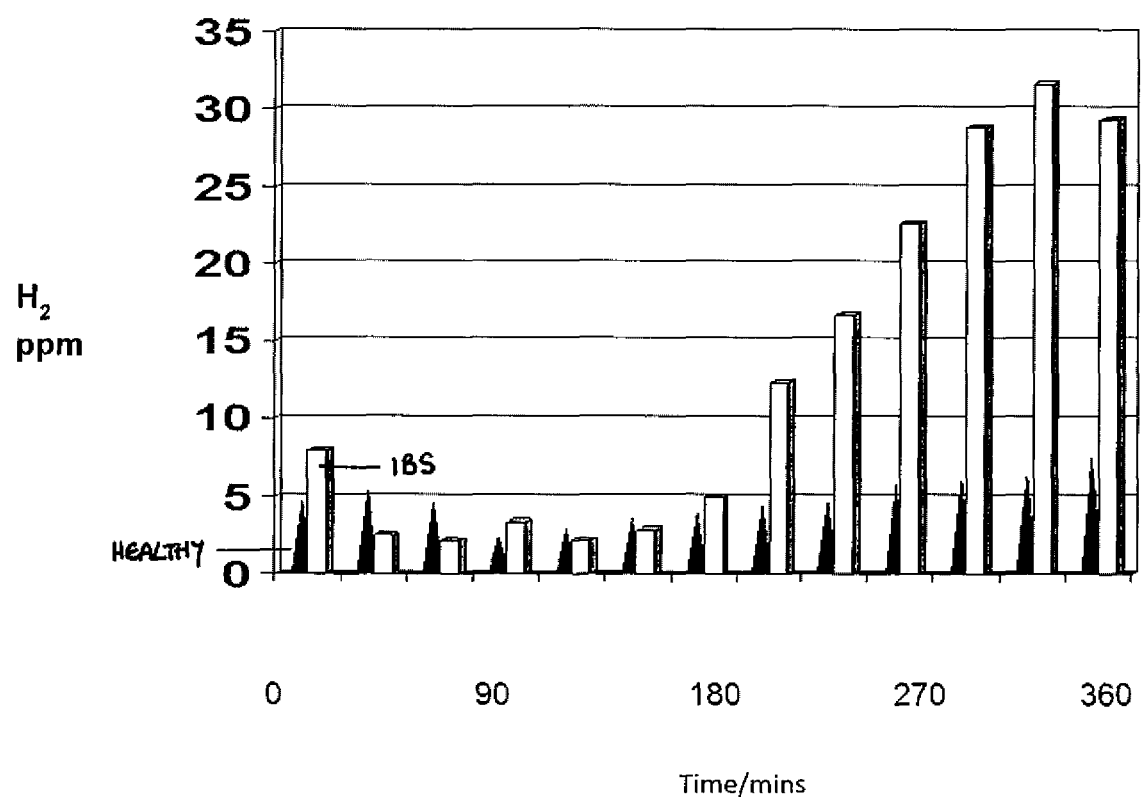

ENZYME COMPOSITIONS AND DIAGNOSTICS FOR USE IN ENTEROMETABOLIC DYSFUNCTION

RELATED APPLICATIONS

This application is a national phase application filed under 35 USC § 371 of PCT Application No. PCT/GB2017/052481 with an International filing date of Aug. 23, 2017, which claims priority of GB Patent Application GB1614415.6 filed Aug. 24, 2016. Each of these applications is herein incorporated by reference in its entirety for all purposes.

FIELD OF THE INVENTION

The invention relates to compositions comprising enzyme-rich malt extracts and/or other digesting enzymes concerning the gut, including carbohydrases, for use in effectively treating enterometabolic disorders such as IBS, IBD and/or enterometabolic syndromes, such as obesity and related disorders such as type II diabetes. The invention extends to in-vitro diagnostic methods for determining enterometabolic disorders/disease such as IBS and IBD, where such enzymes are critical in those disease pathways.

BACKGROUND

Gastrointestinal health has been an area of increasing concern in the last 25 years; frequent and unpleasant symptoms such as abdominal pain, wind, diarrhoea, constipation, headaches, limb and joint pain and lethargy have been reported by patients but no clear and direct cause has been identified by clinicians.

It was often noted that patients reported such symptoms following consumption of particular foodstuffs particularly cereals containing gluten, dairy, caffeine-based beverages or citrus fruits.

Specific food allergies are well recognised, the consumption of a particular food such as shell-fish, nuts or eggs resulting in a clear reaction between specific IgE antibodies in the blood and the relevant food. However, patients describing the aforementioned symptoms often had no such reactive antibodies in their blood.

Patients experiencing these symptoms without evidence of IgE mediation were therefore deemed by clinicians to be suffering "intolerance" to one or more of said foods, rather than allergy; it was also possible that in some patients the symptoms might be psychological in origin.

Irritable bowel syndrome (IBS) is a term that has been used to label a group of symptoms (abdominal pain, wind, diarrhoea, constipation, and headaches) associated with food intolerance. No pathological abnormality is confirmed in routine testing. Nevertheless, these symptoms frequently continue, accounting for as many as 50% of referrals to gastroenterologists. This problem constitutes a significant issue in gastrointestinal health and has been the subject of significant investigation.

One proposal has been that a lack of fibre in the diet and/or increased mental anxiety in work and daily life has led to IBS in British society and for a time a high fibre diet was suggested to patients.

However, it was established by the present inventors during the 1980s that diets of low fibre were actually more successful, the high fibre diets often worsening symptoms.

Instead a review of various other dietary restrictions was developed to deal with IBS and its relationship to intolerance of certain foods. After being accepted by the medical profession, various differing regimes featuring certain food restrictions are now being recommended by clinicians.

The present applicant has continued to investigate a number of links between the physiology of the gut and digestion and how this might impact food intolerance and its relevance to the symptoms experienced in IBS (and to other disorders such as obesity that may be mediated by changes in the gut flora).

One such investigation concerns abnormal break-down of food residues by the microbiome (microbes of the lower GI tract). This study looked at how the excretion of microbial products was affected by changes in diet and specifically reviewed the difference in excretion of hydrogen, short-chain fatty acids (SOFA) e.g. butyrate, propionate, acetate etc., alcohols, fatty acid esters and indoles. A difference was noted; chemical excretion being reduced in urine and faeces by diet, antibiotics or fibre-free liquid/food. It has also been noted that thin mice become fat when given a transplant of the gut microflora from fat mice.

The present inventor has since termed non-infective disorders resulting from an abnormal gut flora "enterometabolic disorders".

Since fermentation activity by bacteria was affected by diet, and since improvements to gut health by changing the activity of gut microbiome were considered possible using so-called pro-biotic chemicals, which were marketed as providing a top-up of healthy bacteria to the gut. However, the present inventors found that neither pro-biotics nor pre-biotics were particularly useful in this regard.

Whilst enterometabolic syndromes or disorders could be loosely linked to changes to the microbiome, the mechanisms by which such changes lead or impact enterometabolic conditions or even metabolic syndromes received little further investigation or study.

As it concerns humans, carbohydrate digestion by the human pancreas is not completed in the small intestine and 20-40 g of starch passes in to the large intestine each day. The fermentation of starch in the colon is known in normal health to be beneficial producing nutritionally valuable SCFAs.

Although changes to the levels of chemical excretions, such as SCFAs, have been broadly linked to the gut flora modification, the mechanisms pertaining to the gut microbiome have only recently been re-examined. At present, however, there is still no clear treatment regime based on a sound scientific rationale for sufferers of enterometabolic disorders, nor for other disorders believed to be linked to a change in the gut flora. Examples of such disorders include IBS, Irritable Bowel disease (IBD) diabetes, obesity, and cancer of the colon, Crohn's disease and the like.

There is a clear need for a new treatment which can be shown to reduce or alleviate the symptoms of these diseases and to treat such disorders more successfully in humans.

SUMMARY OF INVENTION

The present invention concerns a composition comprising a therapeutic amount of enzymes including at least carbohydrases for medical use in humans. The enzymes may include amylase(s) and related enzymes, including fructanases and glucosidases.

Surprisingly, following a confirmation in patient trials, the applicant has found that an enzyme-rich malt extract composition comprising digestion enzymes and including at least carbohydrases has, for the first time, been identified as therapeutically beneficial in humans.

In one embodiment, the composition of the invention comprises a therapeutic amount of enzyme-rich components in accordance with the above disclosures for treatment of disorders arising from an excess of carbohydrate in the gut. In a further embodiment, the composition increases carbohydrate digestion in the gut. In yet a further embodiment the composition reduces fermentation activity of the microbiome.

In one aspect, the present invention concerns a composition, as defined above, for the treatment of enterometabolic disorders.

Although high-calorie diets must play an important part in the development of metabolic disorders such as obesity, (for example, thin mice become fat when given a transplant of the gut microflora from fat mice) it has only become clear that from a consideration of both the applicant's clinical human studies and recent related investigations in rodent models that the gut microbiota also play a significant role in the mechanistic pathways of metabolic syndromes.

It is known that SCFAs, which act at the free fatty acid receptor (FFAR) G-protein-coupled receptors, enhance the secretion of anorectic hormones and increase the feeling of 'fullness' after a meal. Thus, the presence of SCFAs in the gut is generally useful and not necessarily expected to be a target for therapy in this area.

However, acetate (a SOFA) has recently been shown to have a direct role in central appetite regulation. In particular, these recent rodent studies have now been able to explain how and why biological mechanisms and feedback systems associated with common metabolic disorders might result from an increase in acetate production, when induced by diet change. In particular, increased production of acetate from alterations in the gut microbiota in rodents leads to interaction with the gut-brain axis and subsequent obesity.

The applicants believe this mechanism (defined in the rodent model) may also occur to a significant extent in humans, thus the applicant strongly believes that to increase SOFA production without increasing acetate levels would be useful in the treatment of both enterometabolic disorders and metabolic syndromes. In particular, also decreasing other toxic chemicals such as indoles, ethyl esters of fatty acids and alcohols may be useful.

It is noteworthy that previous original work by the applicants and their collaborators led to an understanding that the provision of several different digesting enzymes together as a supplementary feed aids digestion in horses. Extracts of enzyme-rich malted barley (ERME), a source of the desired enzyme combination, was utilised, at that time, to improve the health of the animals and proven do so. This previous research in equine studies "Characterisation of the faecal metabolome and microbiome of Thoroughbred racehorses by C. J. PROUDMAN et al. Equine Veterinary Journal ISSN 0425-1644 DOI: 10.1111/evj.12324" showed a clear reduction in acetate production, following the enzyme-rich malt extract supplemented diet, see FIG. 1.

The applicants therefore consider that empirical studies around compositions which act to reduce acetate levels provide evidence that these compositions are scientifically plausible for the treatment of non-infective disorders originating from, exacerbated or worsened by an imbalance or mal activity of the gut flora.

Unexpectedly, using ERME (for example) as a source of enzymes including carbohydrases in humans would therefore potentially give the desired changes to microbial metabolites without any increase in acetate. On this basis, the applicant was prompted to further investigate whether changing the diet to alter the gut microbiota in man with ERME would have similar effects to those found in horses i.e. an indication from key chemical indicators that such an effect also takes place.

The applicant believes that studies disclosed herein have now successfully demonstrated that the composition of the invention will be clinically useful in humans, particularly treatment for combating enterometabolic disorders, gut dysfunction and metabolic syndromes such as obesity, as well as the systemic inflammation associated with metabolic syndromes. In one embodiment of the invention, the metabolic syndrome is obesity.

The applicant has also conducted successful clinical trials to demonstrate the reduction or clearance of symptoms associated with food intolerances in humans; in particular those disorders that originate from excess starch in the gut and/or related enterometabolic disorders, for example, IBS have been conducted. In one embodiment, the enterometabolic disorder is IBS.

The literature suggests that disorders immediately associated with the mal activity of bacteria may be treated by a composition which is proven to change metabolites produced in the gut for positive health effect. (Van der Waaij L A, Kroese F G, Visser A, Nelis G F, Westerveld B D, Jansen P L, Hunter J O. Immunoglobulin coating of faecal bacteria in inflammatory bowel disease. Eur. J. Gastroenterol. Hepatol. (2004) 16, 669-74) and (Walton C, Fowler D P, Hunter J O et al, Analysis of volatile organic compounds of bacterial origin in chronic gastrointestinal diseases. Inflammatory Bowel Diseases (2013) 19, 2069-2078). Therefore, in a further embodiment, the disorder may a chronic gastrointestinal disease such as IBD.

It follows that such treatment may also be useful in alleviating symptoms associated with other well-known metabolic syndromes or directly treating those disorders. In one embodiment, the composition of the invention comprises a therapeutic amount of enzyme-rich components in accordance with the above disclosures for treatment of diabetes mellitus II and/or insulin resistance.

Literature concerning bowel or colon cancer known in the art would suggest the invention applicable for the use in both the screening of and or treatment of such disorders (Batty C A, Cauchi M, Lourenco C, Hunter J O, Turner C. Use of the analysis of the volatile faecal metabolome in screening for colorectal cancer PLoS, (2015) 10, 1-14 dd:10.137/journal-.pone.0130301).

The invention also extends to the treatment of related disorders such as Crohn's disease where changes in metabolic activity have been shown to impact such disease. (Walton C, Montoya M P B, Fowler D P, Turner C, Jia W, Whitehead R N, Griffiths L, Waring R H, Ramsden D B, Cole J A, Cauchi M, Bessant C, Naylor S J and Hunter J O. Enteral feeding reduces metabolic activity of the intestinal microbiome in Crohn's disease: an observational study European Journal of Clinical Nutrition (2016) 1-5; doi: 10.1038/ejcn.2016.74)

It seems probable that the invention will prove of great value in helping to control the symptoms of entero-metabolic disorders even when these may have very different clinical presentations, including and extending to such conditions as, for example, rheumatoid arthritis and immune thrombocytopaenic purpura.

The invention may therefore be further extended to any other enterometabolic disorder, such as immune thrombocytopaenia (ITP) or rheumatoid arthritis, where changes in metabolic activity have been shown to impact such disease and therefore could be treated by a composition which is proven to change metabolites produced in the gut for positive health effect. (Batty C A, Cauchi M, Hunter J O, Woolner J, Baglin T, Turner C. Differences in microbial metabolites in urine headspace of subjects with immune thrombocytopaenia (ITP) detected by volatile organic compound (VOC) analysis and metabolomics. Clinica Chemica Acta (2016) 461, 61-68 and Kavanagh R, Workman E, Nash P, Smith M, Hazleman B L, Hunter J O The effects of elemental diet and subsequent food reintroduction on rheumatoid arthritis British Journal of Rheumatology (1995) 34, 270-3). In particular, the enzyme-rich composition may be derived from the enzyme-rich extracts of malted barley.

The combination of such enzymes may be obtained from more than a single source or from a different source such as bacteria.

Preferred formulations of the invention include one or more pharmaceutically acceptable excipient. The composition may further comprise with one or more bulking agents, stabilisers, thickeners, additional vitamins, minerals, edible oils (such as linseed oil), salts and/or electrolytes. It may be provided as a liquid, powder or moist product. It may be added to drinking water.

In a preferred embodiment the invention concerns a composition comprising an enzyme rich malt extract including carbohydrases for medical use, wherein the dosage in 20-40 ml given twice daily.

In one embodiment the composition is given in the form of a food supplement suitable for humans.

In a further embodiment, the invention concerns a food for medical purposes comprising any of the compositions previously disclosed.

The invention also extends to a method of medical treatment comprising administering any of the previously disclosed compositions to a human in need of treatment. In preferred embodiments the treatment is for an enterometabolic disorder, IBS, IBD, diabetes mellitus II, insulin resistance, colon cancer and/or Crohn's disease.

In a further aspect the invention extends to an in-vitro diagnostic method of diagnosing an enterometabolic syndrome in a human subject, the method comprising; measuring a first baseline hydrogen breath excretion amount (HBE1) in a breath sample from the subject following a fasting period, measuring a second hydrogen breath excretion amount (HBE2) in a breath sample from the subject, at least 180 minutes following ingestion of carbohydrate food stuff by the subject; determining the difference between the first and the second amounts of hydrogen in breath excretion, wherein an enterometabolic disorder is diagnosed when that difference is a statistically relevant increase in the amount of hydrogen excreted. In some examples, measuring the second hydrogen breath excretion amount occurs at 210 minutes, 240 minute, 270 minutes, 300 minutes and more preferably 330 minutes or 360 minutes, after measuring the first baseline hydrogen excretion amount. The carbohydrate food stuff is typically in the range of 30-90 g, and preferably about 60 g and/or the carbohydrate food stuff is bread.

In examples, the enterometabolic disorder is IBS, or IBD.

BRIEF DESCRIPTION OF THE DRAWINGS

The invention will now be described by way of example only with reference to the following figures:

FIG. 1: shows acetate reduction from the applicant's previous work in Equine studies FIG. 2: graph illustrating hydrogen exhalation during preliminary human IBS trial with ERME FIG. 3: graph illustrating hydrogen exhalation during follow up human trial of IBS and healthy subjects, with and without ERME treatment FIG. 4: graphical analysis of Hydrogen exhalation of IBS vs healthy subjects, without ERME

DETAILED DESCRIPTION

The applicant has previously hypothesised, as described above, that individuals with a low concentration enzymes, necessary to breakdown food residue, may be suffering a disorder of bacterial fermentation in the colon i.e. an enterometabolic dysfunction, where and in which the gut flora is abnormal. In enterometabolic disorders, it is likely that aerobic bacteria survive in a part of the gut which is low in oxygen. Their numbers increase by two orders of magnitude ($10^7$ to $10^9$).

The applicant, taking inspiration from the associated and successful veterinary work described above, investigated whether the provision of a combination of digesting enzymes found in ERME, such as amylase(s) or, similar (and perhaps optimised for human health considerations) could be medically beneficial in the human gut and useful in alleviating or preventing disorders associated enterometabolic characteristics.

This surprising use of a composition comprising digesting enzymes from (e.g. from enzyme-rich malted barley extract and including carbohydrate digesting enzymes) could not have been foreseen as being particularly advantageous in human health, whether for metabolic syndrome, enterometabolic disorders, or other conditions, illnesses, and diseases.

Metabolic syndrome, which is associated with obesity, inflammation, Type 2 diabetes and other endocrinopathies, is believed to be triggered by metabolic endotoxaemia with an increase in plasma LPS levels. Metabolic endotoxaemia, in turn, is thought to be due to a pathogenic gut microbiota. In a study of 140 patients in intensive care with severe systemic inflammatory response syndrome (SIRS), it was found that their concentrations of faecal SCFAs (butyrate, propionate, acetate) were lower than in those in controls; those with gastrointestinal complications had the lowest values. Similarly, patients with bowel cancer had lower butyrate than controls but higher levels of acetate. These findings are consistent with that lactate and SCFAs down-regulate the pro-inflammatory responses in intestinal epithelial cells. Clearly, gut and systemic inflammation are associated with low SCFAs. Therapeutic intervention based on providing these compounds has previously been hypothesised as potentially useful on this basis.

Until very recently little information was available about the mechanisms confirming the direct link between metabolic syndromes or disorders and changes to the gut microbiota No studies had been conducted concerning the enzyme concentrations and the colonic flora.

However, as previously alluded to, there is now highly relevant scientific rationale (e.g., Acetate mediates a microbiome-brain-β-cell axis to promote metabolic syndrome, Perry et al. Nature 10.1038/nature18309) which, in addition to the applicant's clinical studies provided herein, provides further support to the applicant's assertions herein.

The above-mentioned paper coherently demonstrates that the gut microbiota, when altered by diet, leads directly to an increased endogenous production of acetate and a marked increase in acetate turnover and faecal excretion. This paper reports the mechanistic interactions that are considered to result from that increased acetate production; importantly, rodent studies demonstrate that parasympathetic nervous system activation associated with this acetate increase (and resulting directly from high fat/calorie dense diets) increases glucose-stimulated insulin secretion and ghrelin secretion and generates a positive feedback loop leading to hyperphagia, hypertriglyceridaemia, ectopic lipid deposition in liver and muscle, and liver- and muscle-associated insulin resistance.

The present authors support that should the gut flora be altered (e.g. by chronic exposure to a calorie dense diet) the microbiome in humans could have a similarly increased acetate turnover. The applicant considers this document provides a reasonable biological rationale to support the need to reduce acetate turnover in order to treat conditions where the gut flora is altered and/or functioning insufficiently or and/or undesirably.

The previous work by the applicants and their collaborators showing that additional dietary digesting enzymes from extracts of malted barley reduce in acetate production in animals has therefore provided motivation to undertake the first of several clinical trials to confirm the hypothesis that such enzyme-based compositions would also benefit the health of the human gut.

Preliminary Study

The applicant first conducted a specific trial to investigate whether compositions comprising enzyme compositions of the present invention, such as enzyme-rich malt extract, had an effect on digestion, particularly carbohydrate digestion, in symptomatic humans by measurement of hydrogen release on the breath.

Participants:

A preliminary investigation on 3 patients aged 22-63 all with clinically diagnosed IBS were treated with a composition comprising either a control or a dosage of ERME of 20-40 ml.

Exclusion criteria for participation in the study included: pregnancy and lactation; smoking or vaping, course of antibiotics in the previous 6 weeks, chronic medication (except oral contraceptives), food poisoning or gastro-enteritis in previous six weeks, Coeliac disease, Crohn's disease, lacking full mental capacity, prisoners.

ERME Preparation

Enzyme-rich malt extract (ERME) supplied as 80% protein solids, with no added components: 30 mls dose supplied by Muntons, Maltsters of Stowmarket, Suffolk.

Control:

A malt extract of similar flavour in, which the enzymes have been destroyed by heating, served as a control.

Method

Subjects fasted overnight and then two fasting breath hydrogen determinations are made to obtain baseline measurements. Subjects ingested, over 15 minutes, two slices of whole-meal bread and one bagel with ERME. Hydrogen determinations were taken every 30 mins thereafter for a total of 6 hours.

A repeat study was performed 2 weeks later using the alternative control malt extract.

Hydrogen Levels

Chemical analysis: hydrogen excreted on the breath was measured using a hand-held breath analyser (e.g. Gastrolyser, Bedfont UK). Specific food residues are broken down by colonic microflora and produce chemicals e.g. SCFAs, ammonia, hydrogen and carbon dioxide. Hydrogen, in particular, can be detected in the exhaled breath over the course of 6 hours. Foods such as potato, corn or whole wheat result in considerable increases in hydrogen.

Results

Significance is calculated using standard statistical tests and a value of $p<0.05$ accepted as significant.

All subjects reported significant improvement of symptoms of IBS and in two cases complete relief when ERME was ingested.

The change in breath hydrogen levels, of one of the three subjects during the study, is shown in FIG. 2. The area under the curve has been calculated and compares the levels of hydrogen excreted with and without the composition of the invention: Series 1 (black) shows hydrogen excretion after bread without ERME and Series 2 (grey) shows the hydrogen excretion after bread with ERME.

The applicant notes that food digestion in the human small bowel is incomplete with 20-40 g carbohydrate, 3-4 g fat, 12-14 g protein and 5-20 g of dietary fibre passing from the small to the large bowel each day. ERME clearly made a dramatic difference to the IBS sufferers as no hydrogen appeared after 4 hours and therefore this simple trial provides a useful demonstration on the potential effect of ERME on colonic fermentation and medical treatment applicability.

These preliminary studies show that a therapeutic amount of digesting enzymes, including at least carbohydrases, as provided by ERME, for example, is capable of providing symptomatic improvement in patients with IBS. Its effect on bacterial fermentation in the colon is supported by the dramatic fall in hydrogen release after ERME, compared to that in the control test.

The encouraging results of the trials, together with the supporting evidence for a robust and compelling biological theory for why such a composition would, mechanistically, achieves this desirable, important and unanticipated clinical result in humans, provides a plausible disclosure for the first time that such a composition (which includes a therapeutic amount of carbohydrate digesting enzymes) is useful for targets in gut of humans, i.e. as a human medicament in vivo.

Specifically, it is equally plausible that the same composition is useful for treating disorders/diseases (e.g. metabolic syndromes, obesity, diabetes etc.) which concern a target shown to be involved in the mechanism by which diet-microbiota interaction takes place (e.g. carbohydrates to reduce acetate, for example).

Double Blind Study

As discussed, the symptoms of irritable bowel syndrome (IBS) have been shown to be caused by the bacterial breakdown of food residues in the lower gut. Based on the before-mentioned findings of the above studies, the present applicant performed a further test with a bread challenge to review the impact of ERME on both symptomatic IBS patients and healthy subjects.

A double-blind trial was therefore undertaken in which the effect of ingesting 30 mls ERME was compared with a 30 mls control during a bread challenge.

Participants:

Volunteers were Sought from:

patients with IBS which was known to respond successfully to dietary restriction and healthy individuals with no known gastrointestinal problems;

All Subjects Were aged 18-65 not pregnant or lactating had not received antibiotic treatment during the previous six weeks chronic medication, such as oral contraceptives, were allowed provided that they were not changed during the time of the study 10 volunteers were recruited, 5 with food-intolerant IBS and 5 healthy volunteers Control:

An inactivated malt extract of 30 ml (enzyme activity had previously been destroyed by heating) served as a control.

ERME:

Enzyme-rich malt extract (ERME) supplied as 80% protein solids, with no added components: 30 mls dose.

Method:

Each volunteer was asked to eat 2 slices (c.60 g) of wholemeal bread spread with butter together with 30 mls of malt extract (Muntons Ltd, Stowmarket, UK) after an overnight fast on two occasions approximately 2 weeks apart.

On each occasion the malt extract, given double blind, was either ERME (80% protein content) or control.

Symptoms and breath hydrogen concentrations were determined for six hours after a challenge with whole-meal bread and butter.

Chemical Analysis:

Breath hydrogen concentrations were determined using a Bedfont E60 Gastrolyser before eating and at 30 minute intervals thereafter, for a period of six hours, during which no other food was allowed.

Results

Incomplete: 3 patients with IBS withdrew during the study because they feared that taking bread, to which they were intolerant, without ERME protection might upset the delicate balance of their control of IBS symptoms.

Complete: 2 patients with IBS and 5 healthy volunteers completed the study.

Of the completed data it was noted that the average transit time from mouth to caecum was 3.5 hours. After that interval, increasing breath hydrogen release began (FIG. 3).

In 1 healthy male however, the transit time was very much shorter: 2 hours in the first test and less than 30 mins in the second, Furthermore, the levels of breath hydrogen were much greater (reaching 76 ppm). He had an excessively rapid transit time and following a report that he had recently suffered an upset prior to the start of the trial, data was excluded from further analysis.

The mean hydrogen excretions over the six hours of the test are shown below in Table 1 and illustrated in FIG. 3.

TABLE 1

BREATH HYDROGEN CONCENTRATIONS

BREATH HYDROGEN CONCENTRATIONS WITH AND WITHOUT ERME

| TIME | CONTROL | ERME | t | p value |
|---|---|---|---|---|
| 0 | 4.17 ± 3.43 | 4.33 ± 4.63 | 0.071 | 0.94 NS |
| 30 | 4.00 ± 2.83 | 3.50 ± 2.88 | 0.30 | 0.77 NS |
| 60 | 3.83 ± 3.06 | 4.00 ± 3.35 | 0.90 | 0.93 NS |
| 90 | 2.5 ± 2.07 | 2.33 ± 1.21 | 0.17 | 0.87 NS |
| 120 | 2.00 ± 1.55 | 2.67 ± 1.51 | 0.76 | 0.47 NS |
| 150 | 2.83 ± 2.32 | 2.33 ± 1.63 | 0.43 | 0.67 NS |
| 180 | 5.17 ± 3.82 | 4.00 ± 2.10 | 0.66 | 0.53 NS |
| 210 | 7.50 ± 5.89 | 5.17 ± 2.34 | 0.89 | 0.39 NS |
| 240 | 6.50 ± 3.94 | 4.83 ± 3.49 | 0.78 | 0.46 NS |
| 270 | 11.17 ± 6.31 | 4.67 ± 3.01 | 2.28 | 0.05 * |
| 300 | 15.33 ± 10.48 | 3.67 ± 1.86 | 2.68 | 0.02 * |
| 330 | 18.33 ± 12.91 | 6.17 ± 3.60 | 2.22 | 0.05 * |
| 360 | 22.2 ± 12.32 | 4.6 ± 3.29 | 3.08 | 0.015 * |

As can be seen, hydrogen levels remain low for 210 minutes and then rise.

However, hydrogen release after ERME was significantly less than the control at 270, 300, 330 and 360 mins respectively.

In 2 IBS patients and 4 healthy controls, ERME significantly reduced hydrogen breath levels between 270 and 360 minutes after eating.

The 2 IBS patients complained of excess flatulence and abdominal pain on bread and control malt but developed no symptoms after bread and ERME.

Hydrogen release in the normal volunteers provided further insight: 3 of the 4 healthy volunteers all had virtually identical responses to eating bread, whichever malt extract (ERME or control) was ingested. As expected, in a non IBS sufferer, the intrinsic level of amylase in pancreatic secretions appears entirely sufficient for full digestion of the bread, with no extra benefit seen after administration of ERME.

Mean hydrogen excretion was significantly reduced by ERME providing objective proof that it does indeed reduce the amount of starch reaching the lower bowel and prevents symptoms in subjects with IBS. ERME contains high concentrations of starch catalysing enzymes, including amylase, proteases, fructanases and glucanases.

Seemingly, where endogenous pancreatic amylase secretion may be low, in patients suffering from IBS, ERME has been able to pass through the stomach without enzyme de-activation to enable such patients to increases their small bowel digestion under the bread challenge, reducing malfermentation and hence improve IBS symptoms.

In any case it is apparent that a diagnostic test which confirms a sub optimum gut state and thus starch intolerance is useful in the diagnosis of IBS.

Further, a treatment following the diagnosis of IBS and/or similar enterometabolic disorders, in the form of ERME, would also solve the longstanding problem of how to positively identify and treat these types of disorder.

Diagnostics

The applicant believes that these studies support the possibility that IBS and/or IBD may occur as well as being potentially worsened by a change in the gut microbiome.

The applicant has provided further support for this conclusion by undertaking further investigation into this issue:

Diagnostic Support Study

A study was also conducted which compared the hydrogen release following starch digestion of 60 g bread by either IBS patients or healthy subjects, but without treatment of any kind.

Of the 10 patients, 6 were IBS sufferers and 4 were healthy controls.

Exclusion criteria for healthy participants in the study included: pregnancy and lactation; smoking or vaping, course of antibiotics in the previous 6 weeks, chronic medication (except oral contraceptives), food poisoning or gastro-enteritis in previous six weeks, Coeliac disease, Crohn's disease, Irritable bowel syndrome, food allergies or intolerances, lacking full mental capacity, other enterometabolic disorders (e.g obesity, Type 2 diabetes, auto-immune diseases), prisoners.

Chemical Analysis:

Hydrogen excreted on the breath was measured using a hand-held breath analyser (e.g. Gastrolyser, Bedfont UK).

Specific food residues are broken down by colonic microflora and produce chemicals e.g. SCFAs, ammonia, hydrogen and carbon dioxide. Hydrogen, in particular, can be detected in the exhaled breath over the course of 6 hours.

Foods such as potato, corn or whole wheat result in considerable increases in hydrogen.

Method
1. Volunteers fast overnight.
2. At the start of the study, to obtain base line measurements two fasting breath hydrogen determinations are made.
3. Subjects eat, over the course of 15 minutes, two slices of whole-meal bread of approximately 60 g.
4. Breath hydrogen determinations are taken every 30 mins for a total of 6 hours.

Hydrogen Testing and Levels

Hydrogen breath testing was typically used for the diagnosis of inadequate levels of lactase in the small intestine, an enzyme which normally breaks down lactose to glucose and galactose, which are then absorbed. If the enzyme is deficient undigested lactose passes down the small intestine and is metabolised by the colonic microflora releasing hydrogen and usually producing diarrhoea. The release of hydrogen on the breath after the standard dose of lactose is therefore a useful test for this deficiency. Testing of this type has been more widely used after the administration of an oral dose of another sugar, Lactulose, which cannot be digested in the human gut. It thus inevitably passes down the small intestine into the caecum where the bacteria metabolise it releasing hydrogen.

Lactulose testing has been used for multiple purposes; the time taken before hydrogen excretion on the breath commences gives an indication of the transit time between swallowing lactulose and its arrival in the caecum, which may sometimes be clinically valuable. However, it has also been used in patients with IBS. Interpretation of results in this situation is controversial; some authorities recommend treatment of IBS (with high hydrogen excretion after Lactulose) with non-absorbable antibiotics to reduce bacterial activity in the gut. However, as discussed previously, no diagnostic test and/or combined treatment tool, including this suggestion, has proven particularly successful in alleviating IBS.

In the present case the applicant sought to modify the test to confirm a new and different hypothesis. Hydrogen testing has been applied following a different digestive challenge to elucidate whether other mechanistic deficiencies are relevant to IBS and associated enterometabolic disorders and key to identifying treatment.

The test provided for in Table 2, in the present application, is therefore differentiated from the traditional hydrogen tests; herein a measure of the degree of digestion of the starch in the bread by intestinal amylase and related enzymes is elucidated and analysed.

Results

Significance is calculated using standard statistical tests and a value of $p<0.05$ accepted as significant.

The resulting mean hydrogen excretions after 60 g of bread are shown in Table 2:

| Time | Normal Mean ± SD | IBS Mean ± SD | P value |
|---|---|---|---|
| 0 | 4.58 ± 3.84 | 7.92 ± 11.82 | 0.61 |
| 30 | 5.25 ± 2.75 | 2.5 ± 1.97 | 0.10 |
| 60 | 4.5 ± 3.51 | 2.17 ± 2.4 | 0.24 |
| 90 | 2.25 ± 2.63 | 3.33 ± 3.39 | 0.61 |
| 120 | 2.75 ± 1.50 | 2.17 ± 1.83 | 0.61 |
| 150 | 3.5 ± 2.65 | 2.83 ± 2.14 | 0.67 |
| 180 | 3.75 ± 2.22 | 5.00 ± 4.05 | 0.59 |
| 210 | 4.25 ± 1.89 | 12.33 ± 13.00 | 0.26 |
| 240 | 4.5 ± 2.38 | 16.67 ± 25.94 | 0.39 |
| 270 | 5.75 ± 2.06 | 22.67 ± 24.72 | 0.22 |
| 300 | 6.00 ± 3.16 | 28.8 ± 23.87 | 0.099 |
| 330 | 6.25 ± 3.3 | 31.67 ± 15.54 | 0.0133 * |
| 360 | 7.33 ± 5.51 | 29.33 ± 10.46 | 0.0124 * |

In healthy individuals the carbohydrate is completely digested, as shown in FIG. 4. In IBS subjects, digestion is incomplete, resulting in a raised hydrogen emission.

There is a clear difference in hydrogen excretion after 3 hours (and this becomes statistically significant at 330 and 360 minutes).

This baseline direct bread challenge comparison without treatment, in combination with the results in which ERME is provided following a bread challenge further supports the model that IBS patients lack, to a lesser or greater extent, amylase activity sufficient to completely digest the starch.

However, as described in the accompanying subject testing, as shown in FIGS. 2 and 3, treatment with ERME appears to replace that deficiency in the gut, effecting improved digestion and ultimately alleviating IBS, in symptomatic patients.

Sources of Enzyme-Rich Components

ERME

In one embodiment of the invention the enzyme-based composition is derived from enzyme-rich malt extract (ERME).

The compositions of the invention may therefore comprise extracts of malt barley, malt being germinated seed or grain. The seeds are made to germinate by soaking in water and are then usually halted by drying with hot air. Germination causes the seed to produce a variety of enzymes that modify, for example, starches into sugars, through the production of amylases and other carbohydrases, such as fructanases. The germination process also induces other enzymes, such as proteases that break down proteins in the grain.

Conventionally malted grains used in the production of beer, whisky, malted vinegar or malt flavourings, are kiln dried at temperatures up to 90° C. for ales, 80° C. for lagers and lower for malts required to be high in enzyme content. At higher temperatures greater proportions of the enzymes present in the malt are denatured by the heating and drying process.

For example, barley grains are typically grown in a current of cool humidified air and are allowed to germinate ('sprout'). They are then carefully dried ('kilned') and cleaned and the rootlets removed.

The sprouted grains are then milled and water is added at the appropriate temperature to make a mash. The various enzymes present are effective at different temperatures, Therefore the mash is usually started at around 50° C. when proteases and beta amylases break down the ground malt.

The mash temperature is progressively raised to 65° C. when the starch gelatinises and permits degradation to sugars by the action of alpha amylases. After mashing and stirring for around 1 hour the liquid is separated from the residual solids ('spent grain'). The liquid ('wort') is then concentrated by vacuum evaporation to give malt extract, typically 80% solids in solution. Malt extract may be made without active enzymes or as an enzyme-rich extract depending on the temperatures used in evaporation. Enzyme-rich extracts have high diastatic power (high DP)

and the nature of the enzymes is regulated by the nature of the seed, such as barley variety being malted, the growth conditions during germination and by gentler kilning programmes.

The details of the kilning and drying of the malt and of the concentration of the wort determine the colour and flavour of the malt extract and the activity of the enzymes contained in it.

The final malt extract is a sugar-rich solution which may, depending on the process used, contain soluble carbohydrate, peptides, amino acids and a range of enzymes. A high DP extract is used for starch degrading activity and enzymes present typically include amylytic activity with a-amylase, β-amylase, debranching enzymes, a-glucosidase, transglucosylases, and phosphorylases. The extract will also typically have significant levels of peptidases and other proteolytic enzymes.

Fructosyltransferase enzymes are found in grasses and in cereals including barley (Altenbach et al 2005 FEBS Letters 579 (21) 4647-4653) and as well as being involved in fructan synthesis, have glycoside hydrolase activity to degrade fructans to less complex sugars. Barley leaves contain sucrose-fructan 6-fructosyltransferase which may also be found in malt extract. (Briggs D E Bolton C A Brookes P A Stevens R 2009 'Brewing Science and Practice' Woodhead Publishing Abington Hall Cambridge and CRC Press Boca Raton USA, Briggs DE 'Malts and Malting' 1998 Blackie Academic and Professional Publishing London UK).

Prior to heating and drying the malt is called "green malt". This is where the grain has germinated but not yet been dried. Typically, for example, seed is immersed or steeped in water two or three times over a period of two or three days to allow the seeds to absorb moisture and start to germinate. The seeds are usually allowed to sprout and occasionally turned for a period of several, typically 3-6 days. At this stage it is called "green malt". After this stage it would normally be dried for conventional use.

The applicants have appreciated that malted grains of the type described allow the production of a ready source of enzymically active enzymes that would assist in the health of the human gut and are therefore useful in the treatment of conditions related thereto.

The formation of a composition comprising a malt extract, such as ERME, which is rich in the relevant enzymes and enables the ability to increase utilisation of carbohydrates, is therefore effective in the gut of humans. Similarly, a composition comprising a therapeutic amount of digesting enzymes, including at least carbohydrases, i.e. similar mixtures of enzymes to ERME, is therefore also useful in this regard. The composition including malted barley extract comprises a plurality of enzymically active enzymes. That is, the enzymes are still capable of having enzyme activity or a substrate, for example treating starch down into one or more smaller components such as mono- or di-saccharides.

The plurality of enzymes may be carbohydrases, which are capable of breaking down one or more carbohydrates into smaller components, or proteases. The enzymes may be plant derived, for example derived from germinating seeds. The enzymes may be derived from bacterial preparations capable of producing said enzymically active enzymes.

Typically the enzymes are one or more amylases and/or one or more fructanases. Amylases catalyse the breakdown of starch into sugars. α-Amylase breaks starch down. It yields maltotriose and maltose from amylose, or maltose, glucose and limit dextrin from amylopectin. β-Amylase breaks starch into maltose. Both a-amylase and β-amylase are found in seeds during germination. Both α- and β-amylase may be present.

The enzymes are conveniently provided by malt extract. Malt is typically green or high diastatic power (high dp) malt formed from germinated seeds that have not been heated and dried above 40° C. or 50° C. to halt germination, as this often reduces the activity of enzymes remaining after that heating step. Malt heated and dried above 50° C. that temperature has much lower enzymatic activity. Preferably, to avoid destruction of the useful enzymes, ERME is not heated above 40° C. Therefore, enzymes such as fructanase are retained in combination with the amylases in the malt. Typically water is added and heated to approximately 40° C. to form the mash which is separated from the grain. The liquid wort may be evaporated by, for example, vacuum evaporation and the enzyme rich malt extract results, for example in a 65%-80% sugar solution containing the enzymes.

Diastatic power is measured in ° Lintner (° L) or by Windisch Kolbach Units (° WK). A malt with enough power to self-convert into starch has a diastatic power near 35° Lintner. A high diastatic malt typically has a value of above 35° Lintner (94° WK), or typically above 45° L, 50° L, 60° L, 70° L or above 80° L. Potentially any seed may be used to produce the malt. For example, wheat, triticale, sorghum, maize, buck wheat or rice may be used. Barley is typically used as this is regularly used as a source of malt for the brewing industry in many countries.

The invention claimed is:

1. A method comprising:
administering a composition comprising an enzyme-rich extract of malted barley comprising a therapeutic amount of digesting enzymes, including at least carbohydrases, soluble carbohydrate, peptides and amino acids, to a human, and
wherein the digesting enzymes are enzymatically active at the time of administration to the human.

2. The method of claim 1 wherein the human is a human in need of treatment and wherein the treatment is for a condition selected from the group consisting of wind, diarrhea, constipation, reduction of gut microbial metabolites selected from the group consisting of indoles, ethyl esters of fatty acids, alcohols, ammonia and mixtures thereof, reduction of toxic gut microbial metabolites, improving a healthy gut microbiome.

3. The method of claim 1, wherein the human desires to improve their gut health.

* * * * *